United States Patent [19]

von Oppolzer

[11] Patent Number: 5,210,196

[45] Date of Patent: May 11, 1993

[54] CHIRAL SULTAMS

[75] Inventor: Johannes von Oppolzer, Vandoeuvres, Switzerland

[73] Assignee: BP Chemicals Limited, London, England

[21] Appl. No.: 689,839

[22] PCT Filed: Oct. 11, 1990

[86] PCT No.: PCT/GB90/01567

§ 371 Date: May 23, 1991

§ 102(e) Date: May 23, 1991

[87] PCT Pub. No.: WO91/05777

PCT Pub. Date: May 2, 1991

[30] Foreign Application Priority Data

Oct. 12, 1989 [GB] United Kingdom ................ 8923027
Apr. 17, 1990 [GB] United Kingdom ................ 9008620

[51] Int. Cl.⁵ .......................................... C07D 275/06
[52] U.S. Cl. ................................................... 548/207
[58] Field of Search ....................................... 548/207

[56] References Cited

U.S. PATENT DOCUMENTS 3,539,584  11/1970  Suh et al. ........................ 548/207
4,253,865   3/1981  Chan ................................ 548/207

FOREIGN PATENT DOCUMENTS 2105580  9/1972  Fed. Rep. of Germany .

OTHER PUBLICATIONS

Vandewalle et al., Tetrahedron vol. 42, No. 14, pp. 4035–4043 (1986).
Oppolzer et al., Helvetica Chimica Acta, vol. 67, pp. 1397–1401 (1984).
Teeninga et al., J. Org. Chem. (1983), 48, pp. 537–542.
Abramovitch et al., J. Chem. Soc. Perkin Trans., No. 22, pp. 2589–2594 (1974).

Primary Examiner—Joseph Paul Brust
Assistant Examiner—Mary Susan H. Gabilan
Attorney, Agent, or Firm—Brooks Haidt Haffner & Delahunty

[57] ABSTRACT

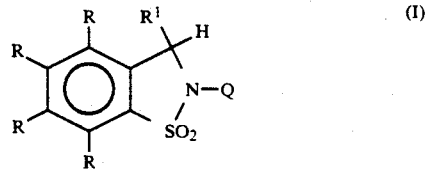

Single enantiomers of chiral sultams having general formula (I), where the R groups are independently hydrogen or $C_1$ to $C_6$ alkyl, and the $R^1$ group is $C_1$ to $C_{20}$ alkyl, in substantially optically pure form are provided. The single enantiomers may be acylated to yield derivatives which are efficient chiral auxiliaries for asymmetric electrophilic substitutions at saturated carbon, Michael additions and Diels-Alder reactions.

2 Claims, No Drawings

CHIRAL SULTAMS

The present invention relates to compositions comprising single enantiomers of certain chiral sultams in substantially optically pure form. The present invention also relates to processes for the preparation of such compositions and to the use of such chiral sultams as chiral auxiliaries i.e. chiral templates on which stereoselective chemical reactions can be carried out.

J Org. Chem 48 537–542 (1983) discloses the preparation of racemic mixtures of 3-substituted 1,2-benzisothiazoline 1,1-dioxides having the formula:

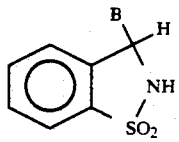

where B is selected from $CH_3$, $C_4H_9$, $i$-$C_3H_7$ and cyclopentyl, by reduction of 3-chloro-1,2-benzisothiazole 1,1-dioxide with sodium borohydride. No use for such compounds is disclosed and, in particular, no attempt was apparently made to resolve the racemic mixture into its constituent enantiomers.

J Chem Soc Perkin 1 2589–2594 (1974) discloses certain 3,3-disubstituted-1,2-benzisothiazoline 1,1-dioxides but these compounds do not possess any chirality. Similar compounds are disclosed in J Chem. Soc 1339 (1952).

A process has now been developed which allows chiral 3-monosubstituted-1,2-benzisothiazoline 1,1-dioxides (hereafter called chiral sultams) to be prepared as single enantiomers with high optical purity. As a consequence of studying the chemistry of the single enantiomers, it has been found that they can function as efficient chiral auxiliaries for a range of prochiral reactants thereby allowing stereoselective chemical reactions to be performed on the prochiral reactant with a range of chiral and achiral reagents. As a consequence such compounds are of great utility in the pharmaceutical and agrochemical industries where it is frequently necessary to carry out highly stereospecific chemical reactions at defined points in the synthesis of a given molecule.

According to the present invention there is provided a single enantiomer of chiral sultam having the general formula:

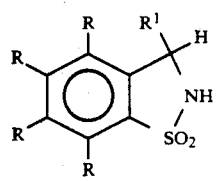

where the R groups are independently, hydrogen or $C_1$ to $C_6$ alkyl and the $R^1$ group is $C_1$ to $C_{20}$ alkyl or aryl substituted alkyl, in substantially optically pure form.

By the term substantially optically pure it is meant that the given enantiomer of the chiral sultam comprises at least 75% preferably at least 90% by weight of the total sample under consideration.

The R groups are preferably selected from hydrogen, methyl, ethyl or propyl. Most preferred are those chiral sultams in which either (a) all the R groups are hydrogen or (b) any three of the R groups are hydrogen and the fourth is either methyl or ethyl.

The $R^1$ group is suitably either an alkyl group or an aryl substituted alkyl group having up to 20 carbon atoms in total. Most preferred are those $R^1$ groups having up to 14 carbon atoms in total. One particularily preferred class of $R^1$ groups is that comprised of $C_1$ to $C_6$ unsubstituted primary alkyl groups and $C_1$ to $C_6$ primary alkyl groups in which the terminal carbon atom is substituted with either phenyl or an alkyl substituted phenyl. Examples of this preferred class include methyl, ethyl, n-propyl, benzyl and 2-phenyl ethyl groups.

Another particularily preferred class of $R^1$ groups is that comprised of $C_1$ to $C_6$ unsubstituted secondary or tertiary alkyl groups and $C_1$ to $C_6$ secondary or tertiary alkyl groups in which the secondary or tertiary carbon atom bonded to the rest of the molecule is substituted with one or more phenyl groups. Examples of this class include iso-propyl, sec-butyl, tert-butyl, $Ph(CH_3)_2C$-$Ph_2(CH_3)C$- (where Ph=phenyl) and the like.

It is believed that the chiral sultams of the present invention other than those where R is selected from methyl, n-butyl, iso-propyl and cyclopentyl, are new compounds.

Single enantiomers of the chiral sultams defined above may be prepared in substantially optical pure form by asymmetric hydrogenation of the corresponding prochiral imine having the formula

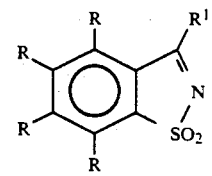

where the R and $R^1$ groups are as defined above.

In an embodiment of the present invention, therefore, there is provided a process for preparing in substantially optically pure form one or other of the enantiomers of a chiral sultam having the formula:

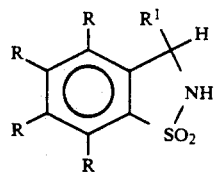

where R and $R^1$ are as defined above which process comprises reacting a prochiral imine of formula:

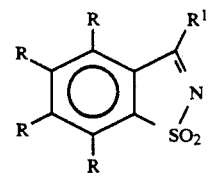

with hydrogen in the presence of an effective amount of a ruthenium containing asymmetric hydrogenation catalyst.

The process defined above is suitably carried out in the liquid phase at a temperature in the range 10° to 60°

C. and at a hydrogen pressure in the range 1 to 10 MPa. Preferred ruthenium containing asymmetric hydrogenation catalysts are those complexes comprised of ruthenium and the single enantiomer of a chiral phosphine. In this respect, particularily preferred chiral phosphines are chiral bidentate phosphines such as 2,2¹-bis(diphenylphosphine-1,1¹-binapthyl), known in the art as BINAP, and ring substituted derivatives thereof. Preferred catalyst precursors include $Ru_2Cl_4(BINAP)_2N(C_2H_5)$, $RuHCl(BINAP)_2$, $Ru_2Cl_4(p\text{-Tol-BINAP})_2N(C_2H_5)_3$ and $Ru_2Cl_4(5\text{-acetylamine BINAP})_2 N(C_2H_5)_3$, $Ru(BINAP)(O_2CCH_3)_2$ etc although the catalyst can also be generated in situ from independent sources of the ruthenium and chiral phosphine. These and other suitable species are described in more detail in EP 245960.

The asymmetric hydrogenation is suitably carried out in an inert solvent or mixture of solvents such as dichloromethane, ethanol and the like. At the end of the reaction, the single enantiomer of the chiral sultam is recovered by known techniques such as chromatography, recrystallisation and the like.

In the case of chiral sultams where the $R^1$ group are either secondary or tertiary alkyl an alternative method of asymmetric hydrogenation is to contact the prochiral imine with lithium aluminiumhydride in the presence or (+)- or (−)-N-methyl-epheridine and 3,5-dimethylphenol in a dry solvent at a temperature in the range −70° to −40° C. If this method is used, the product can be worked up in the usual way.

The prochiral imine defined above can readily be prepared by reacting saacharin or a saccharin derivative of formula:

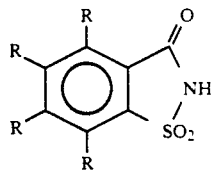

with an alkylating agent. Preferred alkylating agents are (1) those metal alkyls having the formula $R^1_zM$ where $R^1$ is as defined above, M is a Group IA, IIA or IIIA metal and z is an integer corresponding to the oxidation state of M or (2) Grignard reagents having the formula $R^1MgX$ where X is halide. Examples of preferred alkylating agents include $R^1Li$, $R^1MgCl$, $R^1_3Al$, $R^1_3B$ and the like. The process is suitably carried out at a temperature below 0° C. under an inert dry atmosphere such as argon, nitrogen or the like.

As an alternative to the methods described above a racemic mixture of the enantiomers of the chiral sultam can be separated by a process comprising conversion of the mixture to a pair of corresponding diastereoisomers and subsequent fractional crystallisation. An easily separated diastereoisomeric pair can be prepared by reacting the racemic mixture with one or other of the enantiomers of 10-camphorsulphmyl chloride.

It has been found that the single enantiomers of the chiral sultams defined above have the ability to function as efficient chiral auxiliaries for a range of prochiral reactants. In processes which exploit this ability, the chiral sultam is reacted in a first step with an appropriate prochiral precursor to form an educt. The prochiral precursor used is one which can react with the nitrogen atom of the chiral sultam so as to replace the N—H bond with an N—Q bond (Q being a moiety derived from the prochiral precursor). One particularily convenient class of prochiral precursor are acyl halides of formula $R^2COX$ which react with the chiral sultam to produce amide derivatives according to the general equation:

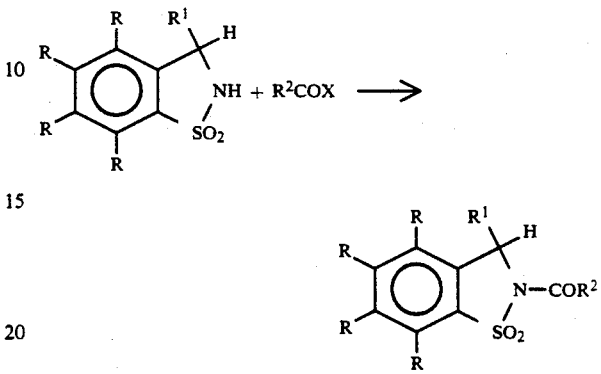

In this equation, X is halide and $R^2$ is a hydrocarbyl group which is both reactive and prochiral at the carbon atom alpha to the carbonyl group. The educt can be isolated if desired of used in situ.

In the second stage of such a process the educt is enolised and then reacted with an appropriate electrophile at the alpha carbon to generate a chiral centre. When this is done, it is found that the electrophile reacts stereoselectively to produce substantially only one of the two possible enantiomers of the product at the new chiral centre notwithstanding the fact that the reagent may not itself possess chirality.

An example of the second step is provided by the reaction of the enolate of educts of formula:

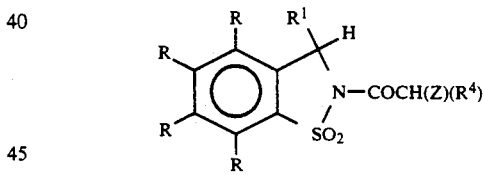

where Z is hydrogen or $C_1$ to $C_{10}$ alkyl and $R^4$ is $C_1$ to $C_{10}$ alkyl, with a range of electrophiles. Thus, reaction with the electrophiles $R^5X$, $R^5COX$, $R^5CHO$ or $R^5COR^5$ where X is halide and the $R^5$ groups are independently any organic group having e.g. up to 50 carbon atoms produces respectively the products where the hydrogen is substituted by $-R^5$, $OCR^5$, $-CH(OH)R^5$ or $-C(OH)R^5R^5$.

The product of the second step can be hydrolysed with base so as to cleave the N—C bond thereby regenerating the chiral sultam and creating selectively a single enantiomer of the carboxylic acid corresponding to the moiety bonded to the nitrogen.

The two steps comprising the process defined above are preferably carried out at temperatures below room temperature under an inert atmosphere in an appropriate dry unreactive solvent such as a halocarbon or ether. The standard techniques of organic chemistry can be used to work up the products at each stage and to isolate desired materials.

A second example of the second step is provided by the asymmetric Michael reaction between an educt having the general formula:

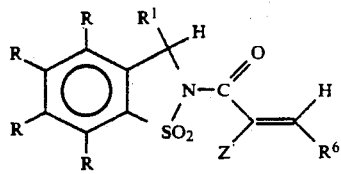

where $R^6$ is $C_1$ to $C_{10}$ alkyl and enolisable compound such as $C_1$ to $C_{10}$ dialkyl malonates, $C_1$ to $C_{10}$ alkyl esters of acetoacetic acid, $C_1$ to $C_{10}$ alkyl esters of cyanoacetic acid and the like. In this class of reactions, the educt is characterised by being prochiral at the beta carbon where reaction occurs. Michael reactions of this type are suitably carried out in the presence of base (e.g. secondary amines, alkali metal alkoxides etc) preferably under an inert atmosphere is a dry unreactive solvent. As with the first example place to yield the corresponding carboxylic acid.

Another example of the second step is provided by the asymmetric Diels-Alder reaction between a cyclic conjugated diene and an educt having the general formula:

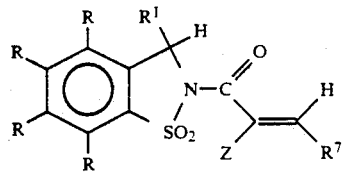

wherein $R^7$ is hydrogen or $C_1$ to $C_6$ alkyl. Thus, where the cyclic conjugated diene is cyclopentadiene there is high selectivity to one of the enantiomers of the product:

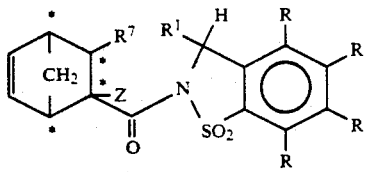

in which chirality is induced at the carbon atoms asterisked. As with the previous example the above mentioned product can be hydrolysed to regenerate the chiral sultam and produce a single enantiomer of the carboxylic acid having the formula:

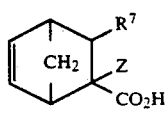

In a further embodiment of the present invention there is therefore provided a process for preparing a single enantiomer of a chiral carboxylic acid having the formula:

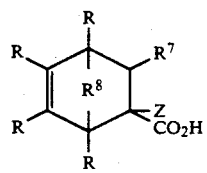

where the R groups are independently as described previously, $R^7$ is hydrogen or $C_1$ to $C_{10}$ alkyl and $R^8$ is —$(CH_2)_n$— where n is 1 to 6, which process comprises (i) reacting a single enantiomer of an educt having the formula:

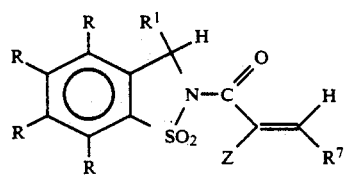

with a cyclic conjugated diene of formula:

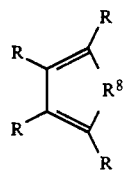

to form a single enantiomer of a product having the formula:

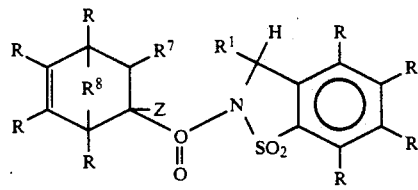

and (ii) thereafter hydrolysing the product to liberate a single enantiomer of a chiral sultam of formula:

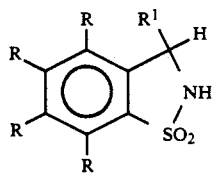

and a single enantiomer of the chiral carboxylic acid.

Step (i) of the process can be carried out under standard Diels-Alder conditions. For this step suitable optional catalysts include Lewis acids derived from aluminium, titanium, boron and tin. Preferred catalysts are alkyl aluminium compounds, the most preferred being the dimethylaluminium halides or the diethylaluminium halides (halide is preferably either Cl or Br). Step (ii) suitably comprises a base catalysed hydrolysis.

EXAMPLE 1

Preparation of the Prochiral Imine (R=H, R$^1$=methyl) from Saccharine

To a solution of o-benzoic acid sulfimide (saccharine) (43.5 g, 240 mmole) in THF (900 ml) at −78 C., was added methyllithium (300 ml of a 1M solution in Et$_2$O, 475 mmole). The solution was stirred overnight at −78° C., thereafter quenched with sat. aq. NH$_4$Cl (400 ml), and the THF removed under vacuum. The aqueous suspension was extracted with EtOAc (3×600 ml), washed with sat. aq. NaCl (200 ml), and the combined extracts were dried (MgSO$_4$). Removal of the solvent gave a pink-white solid (38.2 g, yield-88%), GC(150° C.):5.42 (imine, 100%). By $^1$H-NMR an impurity (5–10%) was detected. This impurity was found to be a dimeric form of the methylated compound. After recrystallisation in MeOH the white crystalline imine in pure form was isolated (33.56 g, 73%), mp=218°-219° C.

IR: 3030, 1565, 1460, 1380, 1345, 1290, 1160. 1H-NMR: 2.65 (s, 3H), 7.7–7.8 (m, 3H), 7.85–7.95 (m, 1H), 13C-NMR: 17.55 (t), 122.23 (d), 124.07 (d), 131.48 (s), 133.80 (d), 133.93 (d), 139.49 (s), 173.17 (s). MS: 181 (C$_8$H$_7$N$_2$S+, 50), 133 (45), 117 (55), 90 (30), 50 (90). HR-MS: 181.0210 I (C$_8$H$_7$NO$_2$S+, calc.=181.0197).

EXAMPLE 2

Preparation of Ru$_2$Cl$_4$[(R)-(+)-BINAP]$_2$(NEt$_3$) Asymmetric Hydrogenation Catalyst To a mixture of [RuCl$_2$(cod)]$_n$ (38 mg, 0.13 mmole) and (R)-(+)-BINAP (90.2 mg, 0.14 mmole) placed in a 250 ml Schlenk tube were added dry and degassed toluene (35 ml) and dry and degassed triethylamine (75 ml, 0.54 mmole) under argon. The brown suspension produced was heated at reflux with stirring for 6 h. The resulting clear solution was cooled to room temperature and the solvent removed under vacuum. The crude product was extracted with degassed CH$_2$Cl$_2$ (3×2 ml) and filtered under argon. Removal of the solvent left anorange crystalline product (123 mg), which was used as catalyst for the hydrogenation step. The product was stored under argon.

EXAMPLE 3

Preparation of the (R)(+) Enantiomer of the Chiral Sultam (R=H, R$^1$=methyl) from the Prochiral Imine of Example 1

Run A: The (R)-(+)-BINAP catalyst of Example 2 (850 mg, 0.49 mmole) was dissolved in CH$_2$Cl$_2$ (10 ml) and then transferred under argon into the reactor (2 l) together with the product of Example 1 (8.14 g, 44 mmole) in solution in dry and degassed ethanol (1000 ml) and CH$_2$Cl$_2$ (500 ml).

Hydrogenation was carried out at 22° C. under 0.4 MPa of H$_2$ for 12 hours. The solvent was concentrated and the catalyst was removed by flash chromatography on SiO$_2$ to give green crystals (6.8 g, yield-84%). After two recrystallisations in hexane/CH$_2$Cl$_2$ the enantiomerically pure sultam (5.8 g, yield-72%) was obtained.

Run B: The (R)-(+)-BINAP catalyst of Example 2 (692 mg, 0.40 mmole) was dissolved in CH$_2$Cl$_2$ (5 ml) and then transferred under argon into the reactor (2 l) together with the product of Example 1 (14 g, 77 mmole) in dry and degassed ethanol (100 ml) and CH$_2$Cl$_2$ (500 ml). The solution was hydrogenated at 22° C. under 0.4 MPa of H$_2$ for 6 days. The solvent was concentrated and the catalyst was removed by a short flash 10 chromatography on SiO$_2$. Two recrystallisations in hexane/CH$_2$Cl$_2$ gave the enantiomerically pure sultam (9.15 g, 65%).

Mp=90.5°-91.0° C., [alpha]$_D$=27.7, (c=1.15, CHCl$_3$, 20° C.). IR: 3360, 3040, 2990, 1455, 1365, 1323, 1300, 1170, 1160, 1135. 1H-NMR: 1.58 (d, J=7, 3H), 4.74–4.90 (m, 2H), 7.40 (d, J=7.5 1H), 7.53 (t, J=7.5, 1H), 7.36 (td, J=7.5,1.0, 1H), 7.77 (d,J=8, 1H). 13C-NMR: 21.34 (t), 53.31 (d), 121.17 (d), 123.83 (d), 129.16 (d), 133.18 (d), 135.44 (s), 141.66 (s). MS: 183 (C$_8$H$_9$NO$_2$S+,0), 168 (M+-CH$_3$, 4), 150 (2), 120 (2.5), 107 (2.5), 83 (100). HR-MS: 168.0121 (C$_7$H$_6$NO$_2$S+, calc.=168.0119).

EXAMPLE 4

Preparation of the (S)(−) Enantiomer of the Chiral Sultam (R=H, R$^1$=Methyl) from the Prochiral Imine of Example 1

Examples 2 and 3 were repeated except that in Example 2 (S)(−) BINAP was used in place of the (R)(+) enantiomer. The catalyst produced was thus Ru$_2$Cl$_4$[(S)-(−)-BINAP]$_2$(NEt)$_3$ and the corresponding (S)(−) enantiomer of the chiral sultam was produced after hydrogenation of the prochiral imine of Example 1.

EXAMPLE 5

Preparation of N-propionyl [3(R)-3-methyl-2,3-dihydro-1,2-benzisothiazole-1,1-dioxide] (propionyl educt of the (R)(+) enantiomer of the Chiral Sultam (R=H, R$^1$=methyl)

Sodium hydride (680 mg, 15.6 mmole) was added to a solution of the product of Example 3 (1.9 g, 10;4 mmole) in dry THF (10 ml) at 0° C. The mixture was stirred for 1 hr at 0° C. and thereafter propionyl chloride (1.8 ml, 20.8 mmole) was added. After addition the mixture was warmed to room temperature and stirred for a further 16 hours Aqueous saturated NH$_4$Cl was then added and the THF evaporated in vacuo. Extraction with CH$_2$Cl$_2$ followed by evaporation, chromatography (SiO$_2$, hexane/Ethyl Acetate 4:1) and crystallisation from methanol yielded the desired product (2.12 g, 85.5%). M.p.=95° C. [alpha]$_D$−19.5° C. C=1.2 CHCl$_3$).

EXAMPLE 6

Preparation of N-(2S)-2-methyl-3-phenyl [(3R)-3-methyl-2,3-dihydro-1,2-benzisothiazole-1,1-dioxide] by reaction of the enolate of the product of Example 5 with Benzyl Iodide A 1M solution of sodium hexamethyldisilazide (1.15 ml, 1.15 mmoles) was added over 30 min. to a solution of the product of Example 5 (250 mg, 1.045 mmoles) in THF (2 ml) at −78° C. Stirring the mixture at −78° C. for 30 min, addition of benzyl iodide (455 mg, 2.09 mmoles), stirring at −78° C. for 2.5 h, addition of sat. aq. NH$_4$Cl, filtration, shaking with Et$_2$O, washing (H$_2$O) and drying (NaCl) of the organic phase, evaporation, chromatography (SiO$_2$, hexane/EtOAc 9:1) and crystallisation (MeOH) afforded the product (277 mg, 81%), m.p. 73°–75° C.

General Procedure for preparing N-acryloyl and N-crotonyl derivatives of the Chiral Sultams A. Acryloyl Derivatives A mixture of freshly distilled triethylamine and the single enantiomer of the chiral sultam in dichloromethane was cooled to 0° C. and acryloyl chloride was added. The solution was stirred for one hour at 0° C. (or at room temperature if reaction is slow) and was then quenched with water (equal volume to dichloromethane). The organic layer was separated and the aqueous solution was extracted with dichloromethane (3×equal volume to dichloromethane). The combined organics were dried (MgSO4) and the solvent removed to give crude product which was purified by FC and crystallisation.

B. Crotonyl Derivatives

A solution of the single enantiomer of the chiral sultam in THF was added dropwise to a suspension of sodium hydride in THF at room temperature and the solution was stirred for one hour. Crotonyl chloride was then added neat, dropwise, and the mixture was stirred overnight. At the end of this time the reaction was quenched by the addition of water and diethyl ether (equal volumes to THF) to give two-layers which were separated. The aqueous layer was then extracted using further ether (3×equal volume to THF). The combined organic extracts were dried and the solvent was removed to give crude product which was purified by FC and crystallisation.

EXAMPLE 7

Preparation of the N-acryloyl derivative of the R-(+)-Chiral Sultam (R=H$_1$ R$^1$=methyl)

The chiral sultam (600 mg, 3.2 mmol), triethylamine (389 mg, 3.85 mmol) and acryloyl chloride (348 mg, 3.85 mmol) in CH$_2$Cl$_2$ (20 ml) were combined following the protocol described in Method A above to give the R-(−)-acryloyl derivative after recrystallisation from CH$_2$Cl$_2$/hexane (505 mg, 2.13 mmol, 66%), M.p. 102- °C. [Alpha]=17.8°, (c=0.27, T=20° C., CH$_2$Cl$_2$).

EXAMPLE 8

Preparation of the N-Crotonyl derivative of the S-(+)-Chiral Sultam (R=H, R$^1$=methyl)

The chiral sultam (1.0 g, 5.5 mmol), NaH (0.5 g of a 55% suspension, 11.5 mmol) and crotonyl chloride (0.57 g, 5.5 mmol) were combined, using the protocol described above in method B, in THF (40 ml) to give, after recrystallisation from ethanol, S-(+) crotonyl derivative (0.82 g, 3.3 mmol, 60%) in the form of white crystals. M.p. 135°-136° C. [Alpha], =28.9, (c=0.60, T=20° C., EtOH).

Diels Alder reactions between the N-acryloyl/N-crotonyl derivatives and dienes

General procedure I

The sultam and excess diene were combined in dichloromethane solvent and cooled to the temperature stated. A solution of the Lewis acid was then added dropwise by syringe. After the given reaction time, the reaction was quenched at low temperature (unless stated otherwise) by the addition of saturated aqueous ammonium chloride and dichloromethane (each three times the volume of the reaction solution). After vigorous stirring the layers were separated and the aqueous layer was extracted with further dichloromethane (5×20 ml). The combined organic extracts were dried (MgSO4) and solvent was removed to give crude product which was purified by FC.

General procedure II

This procedure was designed to reduce the degree of diene polymerisation during the reaction; the sultam was dissolved in dichloromethane and cooled to the given temperature, at which point the appropriate quantity of Lewis acid was added in solution. The diene was then added dropwise in the form of a dilute solution in dichloromethane over a period of 30 to 60 minutes. After full addition the reaction mixture was stirred for the stated time and then quenched and worked up in the way described above for general procedure I.

EXAMPLE 9

Reaction between the product of Example 7 and cyclopentadiene

The product of Example 7 (380 mg, 1.60 mmol) and cyclopentadiene (1.0 g, 15.1 mmol) were combined in dichloromethane (5 ml) and cooled to −98° C. A solution of Me$_2$AlCl (1.0 M$_g$ 3.2 ml, 3.2 mmol) was added dropwise over one minute. By TLC the reaction was complete after ten minutes and was therefore quenched and worked up in the manner described in procedure I. After FC (gradient, elution begins at 3:1 hexane:ethyl acetate) and recrystallisation from dichloromethane/hexane the desired product was isolated at the form of white crystals (399 mg, 1.32 mmol, 83%). HPLC (hexane:ethyl acetate 95:5, 2 ml/min): product after FC; 20.7 (0.26, exo), 25.12 (1.52, endo), 25.81 (78.73, endo), hence 96% d.e. endo: After recrystallisation; 27.55 (100, endo), hence 100% d.e. endo (comparison made in each case with authentic diasterioisomer mixture). M.p. 167°-169° C. [Alpha]=−187.3 (c=275, T=20.1° C., CH$_2$Cl$_2$).

EXAMPLE 10

Hydrolysis of the product of Example 9

Following the literature precedent the product of Example 9 (40 mg, 0.40 mmol) was treated with LiOH (7 mg, 0.27 mmol) and hydrogen peroxide (88 μl of a 30% solution, 27 μl of H$_2$O$_2$, 0.78 mmol) in THF (2.5 ml) and water (1 ml) at 0° C. for two hours. At the end of this time the reaction was quenched using 1.1 eq. of 1.5M Na$_2$SO$_3$. The THF was removed in vacuo and the sultam was extracted with dichloromethane (2×5 ml). The solution was acidified to ph 1 and extracted again with dichloromethane (5×10 ml). Solvent was removed from the initial extracts to give the original sultam (13.1 mg, 0.072 mmol, 55%). Solvent was removed from the second set of extracts to give the carboxylic acid contaminated by a small amount of the chiral sultam (17.6 mg, total: acid 14.7 mg, 0.11 mmol, 82%: sultam, 2.9 mg, 0.016 mmol, 12.2%). The carboxylic acid could be completely freed from the sultam by an exhaustive series of acid/base extractions.

I claim:

1. Substituted Chiral sultam having the general formula:

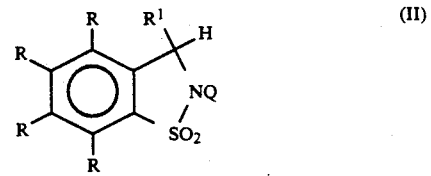

where the R groups are independently hydrogen or C$_1$ to C$_6$ alkyl, R$^1$ is C$_1$ to C$_{20}$ alkyl or aryl substituted alkyl and Q is selected from —OCCH(Z)R$^4$ and —OCC(Z)=CHR$^7$ wherein Z is hydrogen or C$_1$ to C$_{10}$ alkyl, R$^4$ is C$_1$ to C$_{10}$ alkyl and R$^7$ is hydrogen or C$_1$ to C$_6$ alkyl.

2. Single enantiomers of the substituted chiral sultams claimed in claim 1 in substantially optically pure form.

UNITED STATES PATENT AND TRADEMARK OFFICE
CERTIFICATE OF CORRECTION

PATENT NO. : 5,210,196

DATED : May 11, 1993

INVENTOR(S) : JOHANNES von OPPOLZER

It is certified that error appears in the above-identified patent and that said Letters Patent is hereby corrected as shown below:

Col. 3, l. 10, the formula should read "(BINAP)$_2$N(C$_2$H$_5$)$_3$"

Col. 5, l. 24, after the word "example" and before the word "place" insert --the N-C bond can be hydrolysed once the Michael reaction has taken--

Col. 7, l. 25, the formula should read "(C$_8$H$_7$NO$_2$S$^+$, 50)"

Col. 7, l. 26, should read --181.0210 (C$_8$H$_7$NO$_2$S$^+$--

Col. 7, l. 59, should read --(6.8 g, yield=84%)--

Col. 7, l. 61, should read "(5.8 g, yield=72%)"

Col. 8, l. 24, should read "(NEt)$_3$)"

Col. 8, l. 38, should read "mmols)"

Col. 9, l. 46, should read "[Alpha]. =+28.9,"

Col. 10, l. 19, change "at" to --in--

UNITED STATES PATENT AND TRADEMARK OFFICE
CERTIFICATE OF CORRECTION

PATENT NO. : 5,210,196
DATED : May 11, 1993
INVENTOR(S) : Johannes von Oppolzer

It is certified that error appears in the above-indentified patent and that said Letters Patent is hereby corrected as shown below:

Col. 10, line 1, change "sultam" to --sultams--.

Signed and Sealed this

Twenty-sixth Day of April, 1994

Attest:

BRUCE LEHMAN

*Attesting Officer*  *Commissioner of Patents and Trademarks*